US006313217B1

(12) United States Patent
Barthel et al.

(10) Patent No.: US 6,313,217 B1
(45) Date of Patent: Nov. 6, 2001

(54) ORGANOSILICON COMPOUNDS, PROCESSES FOR THEIR PREPARATION, AND THEIR USE IN CROSSLINKABLE ORGANOPOLYSILOXANE COMPOSITIONS

(75) Inventors: Herbert Barthel; Johann Schuster, both of Emmerting; Richard Weidner, Burghausen; Michael Stepp, Burghausen; Volker Frey, Burghausen, all of (DE)

(73) Assignee: Wacker-Chemie GmbH, Munich (DE)

( * ) Notice: Subject to any disclaimer, the term of this patent is extended or adjusted under 35 U.S.C. 154(b) by 0 days.

(21) Appl. No.: 09/366,800

(22) Filed: Aug. 4, 1999

Related U.S. Application Data

(62) Division of application No. 08/760,611, filed on Dec. 4, 1996, now Pat. No. 5,977,243.

(30) Foreign Application Priority Data

Dec. 5, 1995 (DE) .............................. 195 45 363

(51) Int. Cl.⁷ ..................................... C08G 77/08
(52) U.S. Cl. .................. 524/588; 524/860; 524/862; 525/477; 525/478; 525/479; 528/31; 528/15; 528/24; 528/39
(58) Field of Search ..................... 524/588, 862, 524/860; 525/477, 478, 479; 528/39, 24, 15, 31

(56) References Cited

U.S. PATENT DOCUMENTS

| | | |
|---|---|---|
| 3,904,583 | 9/1975 | Saunders et al. . |
| 3,933,729 | 1/1976 | Letoffe . |
| 3,983,265 | 9/1976 | Barthel et al. . |
| 4,431,472 | 2/1984 | Holh et al. . |
| 5,011,962 | * 4/1991 | Staiger et al. ..................... 556/453 |
| 5,047,492 | 9/1991 | Weidner et al. . |
| 5,057,151 | 10/1991 | Schuster et al. . |
| 5,282,998 | 2/1994 | Horn et al. . |
| 5,314,979 | 5/1994 | Okinoshima et al. . |
| 5,545,682 | 8/1996 | Kaiya et al. . |
| 5,548,053 | 8/1996 | Weidner et al. . |
| 5,591,797 | 1/1997 | Barthel et al. . |
| 5,661,222 | * 8/1997 | Hare ..................... 525/478 |
| 5,977,243 | * 11/1999 | Barthel et al. ..................... 524/588 |

FOREIGN PATENT DOCUMENTS

| | | |
|---|---|---|
| 2422846 | 11/1974 | (DE) . |
| 3839900 | 5/1990 | (DE) . |
| 3918337 | 12/1990 | (DE) . |
| 4216139 | 11/1993 | (DE) . |
| 4336345 | 4/1995 | (DE) . |
| 0 367 222 A | 5/1990 | (EP) . |
| 0 480 680 A | 4/1992 | (EP) . |
| 0 518 057 A | 12/1992 | (EP) . |
| 0 645 395 A | 3/1995 | (EP) . |
| WO 94 13741 A | 6/1994 | (WO) . |

OTHER PUBLICATIONS

Polymer Journal, vol. 16, No. 6, 1984, Tokyo, Japan, pp. 495–504, Yoshiki Chujo: "Synthesis and Application of Polymerizable Silicone Oligomers From Water Glass".
Z. anorg. allg. Chem. 424, 115–127 (1976) D. Hoebbel, G. Garzo et al., "Gaschromatagraphic and 29Si–NMR Spectroscopic Investigation on Silicic Acid Trimethylsilylesters".
German Application P 44 01 606.9 and English translation thereof.
German Application P 44 05 245.6 and English translation thereof.
Encyclopedia of Polymer Science & Engineering, vol. 15, pp. 218–224.

\* cited by examiner

*Primary Examiner*—Margaret G. Moore
(74) *Attorney, Agent, or Firm*—Brooks & Kushman P.C.

(57) ABSTRACT

The invention relates to aliphatically unsaturated organosilicon compounds having 2 to 17 silicon atoms, to processes for their preparation and to their use in crosslinkable organopolysiloxane compositions, especially in compositions which can be crosslinked peroxidically or by hydrosilylation.

28 Claims, No Drawings

ORGANOSILICON COMPOUNDS, PROCESSES FOR THEIR PREPARATION, AND THEIR USE IN CROSSLINKABLE ORGANOPOLYSILOXANE COMPOSITIONS

This is a divisional of Ser. No. 08/760,611, filed Dec. 4, 1996, now U.S. Pat. No. 5,977,243.

FIELD OF INVENTION

The present invention relates to organosilicon compounds, to processes for their preparation and their use in crosslinkable organopolysiloxane compositions.

BACKGROUND OF INVENTION

Organosilicon compounds consisting of tetrafunctional units (Q units) of the structure $SiO_{4/2}$— and monofunctional units (M units) of the structure $R_3SiO_{1/2}$—, for example $(Me_3SiO)_4Si$, $(Me_3SiO)_3SiOH$, $(vinyl-Me_2SiO)_4Si$, $(Me_3SiO)_2vinyl-SiOH$ and $(Me_3SiO)_2MeSiOH$ are already known. The preparation of such compounds is also known, by aqueous-alkaline degradation of silica gels, precipitated or pyrogenic silicas with alkylammonium hydroxides, followed by trimethylsilylation. Reference is made, to D. Hoebbel et al., Z. anorg. allg. Chem. 424 (1976) 115.

DE-A-42 16 139 (Wacker-Chemie GmbH; published on Nov. 18, 1993) and corresponding U.S. Pat. No. 5,548,053, describe MQ resins having a ratio of M units to Q units of less than or equal to 1. These MQ resins can be used in place of hydrophobicized highly disperse silicic add as fillers in silicone rubber. DE-B 24 22 846 (Rhône-Poulenc S. A.; published on Apr. 23, 1976) and the corresponding U.S. Pat. No. 3,933,729 and U.S. Pat. No. 3,983,265 describe condensation-crosslinkable organopolysiloxane compositions which for improved adhesion comprise from 10 to 50 parts of MQ resin with a ratio of M units to Q units of less than or equal to 1.2.

SUMMARY OF INVENTION

In the present invention the term organopolysiloxanes is intended to include dimeric, oligomeric and polymeric siloxanes.

The present invention provides organosilicon compounds having 2 to 17 silicon atoms, comprising units of the formula

where
R is identical or different and is a hydrogen atom or optionally substituted, SiC-bonded aliphatically saturated hydrocarbon radical of 1 to 18 carbon atoms, where not more than one radical R per silicon atom can have the meaning of hydrogen atom,
$R^1$ is identical or different and is a SiC-bonded, aliphatically unsaturated hydrocarbon radical of 2 to 18 carbon atoms,
$R^2$ is identical or different and is a hydrogen atom or optionally substituted hydrocarbon radical of 1 to 18 carbon atoms, which can be interrupted by oxygen atoms,
a is 0, 1, 2 or 3,
b is 0, 1, 2 or 3,
c is 0, 1, 2 or 3,
where the sum of a, b and c in formula (I) is less than or equal to 3 and at least one radical $R^1$ is present per molecule. The organosilicon compounds are compounds comprising units of the formula

where
d is 0, 1, 2 or 3,
e is 1, 2 or 3,
f is 0, 1 or 2 and
the sum d+e+f is equal to 4 and/or compounds of the formula

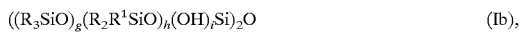

where
g is identical or different and is 0, 1, 2 or 3,
h is identical or different and is 0, 1, 2 or 3,
i is identical or different and is 0, 1 or 2, and
the sum g+h+i is equal to 3 at every silicon atom, and at least one radical $R^1$ is present per molecule.

Radical R is a hydrogen atom and hydrocarbon radicals of 1 to 8 carbon atoms, preferably the methyl radical.

Examples of hydrocarbon radicals R are alkyl radicals, such as the methyl, ethyl, n-propyl, isopropyl, n-butyl, isobutyl, tert-butyl, n-pentyl, isopentyl, neopentyl, tert-pentyl radical, hexyl radicals, such as the n-hexyl radical, heptyl radicals, such as the n-heptyl radical, octyl radicals, such as the n-octyl radical and isooctyl radicals, such as the 2,2,4-trimethylpentyl radical, nonyl radicals, such as the n-nonyl radical, decyl radicals, such as the n-decyl radical, dodecyl radicals, such as the n-dodecyl radical, octadecyl radicals, such as the n-octadecyl radical; cycloalkyl radicals, such as cyclopentyl, cyclohexyl, cycloheptyl radicals and methylcyclohexyl radicals; aryl radicals, such as the phenyl, biphenyl, naphthyl and anthryl and phenanthryl radical; alkaryl radicals, such as o-, m-, p-tolyl radicals, xylyl radicals and ethylphenyl radicals; aralkyl radicals, such as the benzyl radical, the α- and the β-phenylethyl radical.

Examples of substituted hydrocarbon radicals R are halogenated alkyl radicals, such as the 3-chloropropyl, the 3,3,3-trifluoropropyl and the perfluorohexylethyl radical, halogenated aryl radicals, such as the p-chlorophenyl and the p-chlorobenzyl radical.

Radical $R^1$ is alkenyl radicals of 2 to 8 carbon atoms, preferably the vinyl radical.

Examples of radicals $R^1$ are the vinyl, allyl, methallyl, 1-propenyl, 1-butenyl, 1-pentenyl radical, 5-hexenyl, butadienyl, hexadienyl, cyclopentenyl, cyclopentadienyl, cyclohexenyl, ethynyl, propargyl and 1-propynyl radical.

Radical $R^2$ is a hydrogen atom and alkyl radicals of 1 to 8 carbon atoms, preferably hydrogen atom, methyl and ethyl radical, especially hydrogen atom.

Examples of optionally substituted hydrocarbon radicals $R^2$ are the radicals indicated as examples of R and $R^1$ and alkoxyalkyl radicals, such as the methoxyethyl radical and the ethoxyethyl radical.

The organosilicon compounds according to the present invention have a $M_n$ molecular weight of not more than 1000 g/mol, preferably not more than 500 g/mol.

The organosilicon compounds of formula (Ia) according to the present invention are preferably $(R_3SiO)(R_2R^1SiO)_3Si$, $(R_3SiO)_2(R_2R^1SiO)_2Si$, $(R_3SiO)_3(R_2R^1SiO)Si$, $(R_3SiO)(R_2R^1SiO)_2SiOR^2$, $(R_3SiO)_2(R_2R^1SiO)SiOR^2$ and $(R_2R^1SiO)_3SiOR^2$, where R, $R^1$ and $R^2$ have the meaning given above.

The organosilicon compounds of formula (Ia) according to the present invention are preferably $(R_3SiO)(R_2R^1SiO)_3Si$ and $(R_2R^1SiO)_3SiOR_2$, where R, $R^1$ and $R^2$ have the meaning given above.

Examples of the organosilicon compounds of formula (Ia) according to the present invention are $(Me_3SiO)(Me_2$ ViSiO)$_3$Si, Me$_3$SiO)$_2$(Me$_2$ViSiO)$_2$Si, (Me$_3$SiO)$_3$ (Me$_2$ViSiO)Si, (Me$_3$SiO)(Me$_2$ViSiO)$_2$SiOH, (MeSiO)$_2$ (Me$_2$ViSiO)SiOH and (Me$_2$ViSiO)$_3$SiOH, where Me is methyl radical and Vi is vinyl radical.

The organosilicon compounds of formula (Ib) according to the present invention are preferably
(R$_2$R$^1$SiO)$_3$Si—O—Si(R$_2$R$^1$SiO)$_3$,
(R$_3$SiO)(R$_2$R$^1$SiO)$_2$Si—O—Si(R$_2$R$^1$SiO)$_3$,
(R$_3$SiO)$_2$(R$_2$R$^1$SiO)Si—O—SiR$_2$R$^1$SiO)$_3$,
(R$_3$SiO)(R$_2$R$^1$SiO)$_2$Si—O—Si(R$_3$SiO)(R$_2$R$^1$SiO)$_2$,
(R$_2$R$^1$SiO)$_3$Si—O—Si(R$_3$SiO)$_3$,
(R$_3$SiO)(R$_2$R$^1$SiO)$_2$Si—O—Si(R$_3$SiO)$_2$(R$_2$R$^1$SiO),
(R$_3$SiO)$_3$Si—O—Si(R$_3$SiO)(R$_2$R$^1$SiO)$_2$,
(R$_3$SiO)$_2$(R$_2$R$^1$SiO)Si—O—Si(R$_3$SiO)$_2$(R$_2$R$^1$SiO),
(R$_3$SiO)$_3$Si—O—Si(R$_3$SiO)$_2$(R$_2$R$^1$SiO),
(R$_2$R$^1$SiO)$_3$Si—O—Si(R$_2$R$^1$SiO)$_2$(OR$^2$),
(R$_2$R$^1$SiO)$_3$Si—O—Si(R$_2$R$^1$SiO)(OR$^2$)(R$_3$SiO),
(R$_3$SiO)(R$_2$R$^1$SiO)$_2$Si—O—Si(R$_2$R$^1$SiO)$_2$(OR$^2$),
(R$_2$R$^1$SiO)$_3$Si—O—Si(OR$^2$)(R$_3$SiO)$_2$,
(R$_3$SiO)(R$_2$R$^1$SiO)$_2$Si—O—Si(R$_3$SiO)(R$_2$R$^1$SiO)(OR$^2$),
(R$_3$SiO)$_2$(R$_2$R$^1$SiO)Si—O—Si(R$_2$R$^1$SiO)$_2$(OR$^2$),
(R$_3$SiO)(R$_2$R$^1$SiO)$_2$Si—O—Si(R$_3$SiO)$_2$(OR$^2$),
(R$_2$R$^1$SiO)$_2$(OR$^2$)Si—O—Si(R$_3$SiO)$_3$,
(R$_3$SiO)$_2$(R$_2$R$^1$SiO)Si—O—Si(R$_3$SiO)(R$_2$R$^1$SiO)(OR$^2$),
(R$_3$SiO)$_2$(R$_2$R$^1$SiO)Si—O—Si(R$_3$SiO)$_2$(OR$^2$) and
(R$_3$SiO)$_3$Si—O—Si(R$_3$SiO)(OR$^2$)(R$_2$R$^1$SiO),
where R, R$^1$ and R$^2$ have the meaning given above.

The organosilicon compounds of formula (Ib) according to the present invention are preferably (R$_2$R$^1$SiO)$_3$Si—O—Si(R$_2$R$^1$SiO)$_3$, (R$_3$SiO)(R$_2$R$^1$SiO)$_2$Si—O—Si(R$_2$R$^1$SiO)$_3$ and (R$_2$R$^1$SiO)$_3$Si—O—Si(R$_2$R$^1$SiO)$_2$(OR$^2$), where R, R$^1$ and R$_2$ have the meaning given above.

More particular examples of the organosilicon compounds of formula (Ib) according to the present invention are
(Me$_2$ViSiO)$_3$Si—O—Si(Me$_2$ViSiO)$_3$,
(Me$_3$SiO)(Me$_2$ViSiO)$_2$Si—O—Si(Me$_2$ViSiO)$_3$,
(Me$_3$SiO)$_2$(Me$_2$ViSiO)Si—O—Si(Me$_2$ViSiO)$_3$,
(Me$_3$SiO)(Me$_2$ViSiO)$_2$Si—O—Si(Me$_3$SiO)(Me$_2$ViSiO)$_2$,
(Me$_3$SiO)$_3$Si—O—Si(Me$_2$ViSiO)$_3$,
(Me$_3$SiO)$_2$(Me$_2$ViSiO)Si—O—Si(Me$_3$SiO)(Me$_2$ViSiO)$_2$,
(Me$_3$SiO)$_3$Si—O—Si(Me$_3$SiO)(Me$_2$ViSiO)$_2$,
(Me$_3$SiO)$_2$(Me$_2$ViSiO)Si—O—Si(Me$_3$SiO)$_2$(Me$_2$ViSiO),
(Me$_3$SiO)$_3$Si—O—Si(Me$_3$SiO)$_2$(Me$_2$ViSiO),
(Me$_2$ViSiO)$_3$Si—O—Si(Me$_2$ViSiO)$_2$(OH),
(Me$_2$ViSiO)$_3$Si—O—Si(Me$_3$SiO)(Me$_2$ViSiO)(OH),
(Me$_3$SiO)(Me$_2$ViSiO)$_2$Si—O—Si(Me$_2$ViSiO)$_2$(OH),
(Me$_2$ViSiO)$_3$Si—O—Si(Me$_3$SiO)$_2$(OH),
(Me$_3$SiO)(Me$_2$ViSiO)$_2$SiOSi(Me$_3$SiO)(Me$_2$ViSiO)(OH),
(Me$_3$SiO)$_2$(Me$_2$ViSiO)SiOSi(Me$_2$ViSiO)$_2$(OH),
(Me$_3$SiO)(Me$_2$ViSiO)$_2$SiOSi(Me$_3$SiO)$_2$(OH),
(OH)(Me$_2$ViSiO)$_2$SiOSi(Me$_3$SiO)$_3$,
(Me$_3$SiO)$_2$(Me$_2$ViSiO)SiOSi(Me$_3$SiO)(Me$_2$ViSiO)(OH),
(Me$_3$SiO)$_2$(Me$_2$ViSiO)Si—O—Si(Me$_3$SiO)$_2$(OH) and
(Me$_3$SiO)$_3$SiOSi(Me$_3$SiO)(Me$_2$ViSiO)(OH)
where Me is methyl radical and Vi is vinyl radical.

The organosilicon compounds according to the present invention contain at least two radicals R$^1$ per molecule, where R$^1$ has the above meaning.

In order to prepare the organosilicon compounds and/or the organosilicon compounds which are used in accordance with the invention, comprising units of formula (I), procedures which are known in silicone chemistry are used. For example, the organosilicon compounds can be prepared from tetraorganylammonium silicate solutions, as described, in D. Hoebbel et al., Z. anorg. allg. Chem. 424 (1976) 115 ff.

In accordance with the preferred procedure of process 1, in a 1st stage a mixture of monofunctional silanes R$_2$R$^1$SiCl and, optionally R$_3$SiCl, tetrachlorosilane and/or organotrichlorosilane and, optionally organodichlorosilane is reacted with alkanols of 1 to 4 carbon atoms, especially ethanol, at a temperature of from 0° to 80° C., preferably 20° C., and at a pressure of from 900 to 1100 hPa, the reaction mixture is hydrolyzed with the addition of water in a quantity of from 80% to 300% by weight, preferably from 100% to 200% by weight, based on the weight of the reaction mixture, and the resulting siloxanes are isolated from the organic phase, R and R$^1$ having the meaning above.

In the reaction the molar ratio of monofunctional silanes R$_2$R$^1$SiCl and, optionally, R$_3$SiCl to tetrachlorosilane and/or organotrichlorosilane is between 1.6:1 and 10:1, preferably between 1.8:1 and 9:1. Optionally, organodichlorosilane can also be used. If organodichlorosilane is used, then it is used in quantities of not more than 30 mol-%, preferably not more than 20 mol-%, based on tetrachlorosilane and/or organotrichlorosilane.

After the hydrolysis, the aqueous phase is separated from the organic phase and the organic phase is washed to neutrality with water in order to remove any acid still present, the organic phase being freed from non volatile constituents at a temperature of from 80° to 160° C. and a pressure of from 30 to 600 hPa, at a temperature of from 100° to 150° C. and a pressure of from 50 to 500 hPa.

The resulting organosilicon compounds in a 2nd stage, can be reacted with disiloxanes of the formula R$_3$Si—O—SiR$_3$ and/or R$_2$R$^1$Si—O—SiR$^1$R$_2$ and/or R$_3$Si—O—SiR$^1$R$_2$ where R and R$^1$ have the meanings given above in quantities of from 60% to 200% by weight, preferably from 90% to 180% by weight, based on the organosilicon compounds, in the presence of an acidic catalyst at a temperature of from 20° to 200° C., preferably from 40° to 100° C., and at the pressure of the surrounding atmosphere, the acidic catalyst being removed after the end of the reaction.

Examples of the acidic catalysts used in the 2nd stage of process 1, are Lewis acids, such as BF$_3$, AlCl$_3$, FeCl$_3$ and phosphonitrile chloride, and Brönstedt acids, such as hydrochloric acid, sulfuric acid, phosphoric acid, acetic acid and p-toluenesulfonic acid, and acidic ion exchangers, such as zeolites and acid-activated bleaching earth, acid-activated bleaching earth being preferred.

In the 2nd stage of process 1, acidic catalyst is used in quantities of from 1% to 20% by weight, preferably from 2% to 15% by weight, based on the overall weight of the organosilicon compounds used.

After the end of the reaction in the 2nd stage, the catalyst is separated from the reaction mixture by filtration, provided it is a catalyst which is insoluble in the reaction mixture, such as the acid-activated bleaching earth. Otherwise, the catalyst is removed from the reaction mixture by neutralization and subsequent filtration of the resulting saIL The filtrate is then freed from constituents of low volatility at a temperature of from 80° to 160° C. and a pressure of from 30 to 600 hPa, preferably at from 100° to 150° C. and from 50 to 500 hPa.

In accordance with the procedure of process 2, silicon dioxide is reacted with a triorganylsilylation agent in quantities of from 5 to 200 parts by weight, preferably from 20 to 100 parts by weight, based on 100 parts by weight of silicon dioxide, in the presence of aqueous base in quantities of from 0.5 to 200 parts by weight, preferably from 10 to 100 parts by weight, based on 100 parts by weight of silicon dioxide.

The reaction of process 2 is carried out at a temperature of from 0° to 250° C., preferably from 20° to 100° C., and at the pressure of the surrounding atmosphere.

The triorganylsilylation agent which is used in accordance with the invention is $R_3SiOH$ or $R_3SiOSiR_3$, $R_2R^1SiOH$ or $R_2R^1SiOSiR_2R^1$ and $R_3SiNHSiR_3$ and $R_2R^1SiNHSiR_2R^1$.

The aqueous base comprises mixtures of from 5 to 25 parts by weight of ammonia in 100 parts by weight of water. However, the aqueous base can be prepared directly during the reaction by reacting a mixture of water and hexaorganyldisilazane.

Optionally, the reaction can be carried out in an organic solvent which is inert toward the reactants, such as alkanes, aromatic hydrocarbons and halogenated hydrocarbons, or organosilicon compounds which are inert toward the reactants, such as hexamethyldisiloxane.

In process 2, the silicon dioxide used comprises finely divided silicas, silicas produced by wet-chemical precipitation, or silicas produced pyrogenically by flame hydrolysis of, for example, tetrachlorosilane, preference being given to pyrogenically produced highly disperse silicas.

The silicas used in accordance with the invention have a mean primary particle size of not more than 250 nm, preferably not more than 100 nm, more preferably from 2 to 50 nm.

The silicas used in accordance with the invention have a specific surface area (measured in accordance with BET, method according to DIN 66131 and DIN 66132) of more than 25 m²/g, preferably from 50 to 400 m²/g.

After reaction has taken place, after from 0.5 to 60 hours, the highly volatile substances are separated off, optionally with stirring, at a temperature of from 100° to 140° C. and at the pressure of the surrounding atmosphere, and then, at from 140° to 220° C. and at the pressure of the surrounding atmosphere or under reduced pressure, supported optionally by a stream of inert gas, such as nitrogen gas, the organosilicon compounds prepared in accordance with the invention are separated from the residue by distillation.

In the procedure of process 3, in a first stage chlorosiloxanes and/or chlorosilanes, for example those according to DE-A 39 18 337 (Wacker-Chemie GmbH) or the corresponding U.S. Pat. No. 5,011,962, are reacted with siloxanols and/or silanols in the presence of base and, optionally, an organic aprotic solvent, chlorine atoms being replaced by silyl and/or siloxy radicals. If the resulting reaction product still contains Si-bonded chlorine atoms, this product is reacted in a second stage with water in the presence of base and, optionally, of organic aprotic solvent, the Si-bonded chlorine atoms being replaced by Si-bonded hydroxyl groups.

The base used in process 3 comprises organic amines, such as alkylamines, for instance triethylamine, aromatic amines, such as pyridine, and salts thereof, and basic salts, such as sodium hydrogen carbonate and potassium carbonate.

In the first stage of process 3, base is used in a stoichiometric excess of from 0.5% to 300%, preferably in an excess of from 10% to 100%, relative to Si-bonded chlorine.

In the second stage of process 3, carried out optionally, base is used in a stoichiometric excess of from 0.5% to 300%, preferably in an excess of from 10% to 100%, relative to Si-bonded chlorine.

The reaction according to process 3 can optionally be carried out in an organic aprotic solvent which is inert toward the reactants, such as, toluene, cyclohexane, tetrahydrofuran and diethyl ether.

The reaction of process 3 is carried out at a temperature of from −10° C. to 100° C., preferably from room temperature to 80° C., and at the pressure of the surrounding atmosphere.

After reaction has taken place the resulting product is isolated by known methods, such as phase separation, washing to neutrality with water and distillation under reduced pressure.

The organosilicon compounds of the formulae (Ia) and (Ib) are preferably prepared in accordance with process 3.

The organosilicon compounds or those prepared in accordance with the invention, can be used for all purposes for which organosilicon compounds have been used to date.

They are particularly suitable for the preparation of crosslinkable organopolysiloxane compositions.

The present invention additionally provides crosslinkable compositions based on organopolysiloxanes, which in addition to organopolysiloxanes comprise at least one organosilicon compound having 2 to 17 silicon atoms, comprising units of the formula $$R_a R^1_b (OR^2)_c SiO_{4-(a+b+c)/2} \quad (I),$$

where

R, $R^1$, $R_2$, a, b and c have one of the meanings given above, with the proviso that the sum of a, b and c in formula (I) is less than or equal to 3 and at least one radical $R^1$ is present per molecule, preferably at least two radicals $R^1$, more preferably at least three radicals $R^1$, in particular at least four radicals $R^1$.

The organosilicon compounds used in accordance with the invention consists of M units of formula (I), where a+b=3, and Q units of formula (I) where a+b=0, and/or T units of formula (I) where a+b=1.

The organosilicon compounds have a molecular weight of not more than 2500 g/mol, preferably not more than 1000 g/mol, more preferably not more than 500 g/mol.

The organosilicon compounds have a numerical ratio of M units to the sum of the Q units and/or T units of greater than or equal to 2, preferably greater than or equal to 2.5.

The organosilicon compounds preferably contain 4 to 10 silicon atoms.

The organosilicon compounds may comprise a single type or a mixture of at least two different types of organosilicon compounds.

Examples of the organosilicon compounds used according to the invention are $(Me_3SiO)(Me_2ViSiO)_3Si$,
$(Me_3SiO)_2(Me_2ViSiO)_2Si$,
$(Me_2ViSiO)_4Si$,
$(Me_3SiO)(Me_2ViSiO)_2SiOH$,
$(Me_2ViSiO)_3SiOH$,
$(Me_2ViSiO)_3Si$—O—$Si(Me_2ViSiO)_3$,
$(Me_3SiO)(Me_2ViSiO)_2Si$—O—$Si(Me_2ViSiO)_3$,
$(Me_3SiO)_2(Me_2ViSiO)Si$—O—$Si(Me_2ViSiO)_3$,
$(Me_3SiO)(Me_2ViSiO)_2Si$—O—$Si(Me_3SiO)(Me_2ViSiO)_2$,
$(Me_3SiO)_3Si$—O—$(Me_2ViSiO)_3$,
$(Me_3SiO)_2(Me_2ViSiO)Si$—O—$Si(Me_3SiO)(Me_2ViSiO)_2$,
$(Me_3SiO)_3Si$—O—$Si(Me_3SiO)(Me_2ViSiO)_2$,
$(Me_3SiO)_2(Me_2ViSiO)Si$—O—$Si(Me_3SiO)_2(Me_2ViSiO)$,
$(Me_2ViSiO)_3Si$—O—$Si(Me_2ViSiO)_2(OH)$,
$(Me_2ViSiO)_3Si$—O—$Si(Me_3SiO)(Me_2ViSiO)(OH)$,
$(Me_3SiO)(Me_2ViSiO)_2Si$—O—$Si(Me_2ViSiO)_2(OH)$,
$(Me_2ViSiO)_3Si$—O—$Si(Me_3SiO)_2(OH)$,
$(Me_3SiO)(Me_2ViSiO)_2SiOSi(Me_3SiO)(Me_2ViSiO)(OH)$,
$(Me_3SiO)_2(Me_2ViSiO)SiOSi(Me_2ViSiO)_2(OH)$,
$(Me_3SiO)(Me_2ViSiO)_2SiOSi(Me_3SiO)_2(OH)$,
$(OH)(Me_2ViSiO)_2SiOSi(Me_3SiO)_3$
$(Me_3SiO)_2(Me_2ViSiO)SiOSi(Me_3SiO)(Me_2ViSiO)(OH)$,
$[ViMe_2SiO]_2[Me_3SiO]SiMe$,
$[ViMe_2SiO]_3SiMe$,
$[ViMe_2SiO]_2MeSiOH$,

[ViMe$_2$SiO][Me$_3$SiO]$_2$SiVi,
[ViMe$_2$SiO]$_2$[Me$_3$SiO]SiVi,
[ViMe$_2$SiO]$_3$SiVi,
[ViMe$_2$SiO][Me$_3$SiO]ViSiOH and
[ViMe$_2$SiO]$_2$ViSiOH,
where Me is methyl radical and Vi is vinvi radical.

The organosilicon compounds used in accordance with the invention are preferably
(Me$_3$SiO)(Me$_2$ViSiO)$_3$Si,
(Me$_2$ViSiO)$_4$Si,
(Me$_2$ViSiO)$_3$SiOH,
(Me$_2$ViSiO)$_3$Si—O—Si(Me$_2$ViSiO)$_3$,
(Me$_3$SiO)(Me$_2$ViSiO)$_2$Si—O—Si(Me$_2$ViSiO)$_3$,
(Me$_3$SiO)$_2$(Me$_2$ViSiO)Si—O—Si(Me$_2$ViSiO)$_3$,
(Me$_3$SiO)(Me$_2$ViSiO)$_2$Si—O—Si(Me$_3$SiO)(Me$_2$ViSiO)$_2$,
(Me$_3$SiO)$_3$Si—O—Si(Me$_2$ViSiO)$_3$,
(Me$_3$SiO)$_2$(Me$_2$ViSiO)Si—O—Si(Me$_3$SiO)(Me$_2$ViSiO)$_2$,
(Me$_2$ViSiO)$_3$Si—O—Si(Me$_2$ViSiO)$_2$(OH),
(Me$_2$ViSiO)$_3$Si—O—Si(Me$_3$SiO)(Me$_2$ViSiO)(OH),
(Me$_3$SiO)(Me$_2$ViSiO)$_2$Si—O—Si(Me$_2$ViSiO)$_2$(OH),
(Me$_2$ViSiO)$_3$Si—O—Si(Me$_3$SiO)$_2$(OH),
(Me$_3$SiO)(Me$_2$ViSiO)$_2$SiOSi(Me$_3$SiO)(Me$_2$ViSiO)(OH),
(Me$_3$SiO)$_2$(Me$_2$ViSiO)SiOSi(Me$_2$ViSiO)$_2$(OH),
[ViMe$_2$SiO]$_3$SiMe,
[ViMe$_2$SiO]$_2$[Me$_3$SiO]SiVi,
[ViMe$_2$SiO]$_3$SiVi and
[ViMe$_2$SiO]$_2$ViSiOH,
where Me is methyl radical and Vi is vinyl radical.

The organosilicon compounds are preferably [ViMe$_2$SiO]$_3$SiOH, [ViMe$_2$SiO]$_4$Si, [ViMe$_2$SiO]$_3$[Me$_3$SiO]Si, [ViMe$_2$SiO]$_3$SiMe and [ViMe$_2$SiO]$_3$SiVi, where Me is methyl radical and Vi is vinyl radical.

The compositions according to the present invention can comprise any desired, previously known types of organopolysiloxane compositions which can be crosslinked to form elastomers, such as, one-component or two-component organopolysiloxane compositions which vulcanize at room temperature (RTV compositions) or elevated temperature (HTV compositions), where crosslinking can take place by condensation, addition of Si-bonded hydrogen onto aliphatic multiple bond, or peroxidically, by formation of free radicals.

The compositions can be crosslinked by addition of Si-bonded hydrogen onto aliphatic carbon-carbon multiple bond, and organopolysiloxane compositions which can be crosslinked peroxidically.

The nature and quantity of the components used in such compositions are already known. Reference may be made, to German application P44 01 606.9 (Wacker-Chemie GmbH; filed on Jan. 20, 1994), to German application P44 05 245.6 (Wacker-Chemie GmbH; filed on 218.1994) and to DE 43 36 345 A (Wacker-Chemie GmbH; published on Apr. 27, 1995).

The peroxidically crosslinkable organopolysiloxane compositions according to the present invention comprise
(A) organopolysiloxanes comprising units of the formula

(II)

in which
R$^3$ is identical or different and is optionally substituted hydrocarbon radical, and
r is 0, 1, 2 or 3 and has an average numerical value of from 1.9 to 2.1,
(B) reinforcing and/or nonreinforcing fillers,
(C) an agent which brings about the crosslinking, for example organic peroxide,
(D) at least one aliphatically unsaturated organosilicon compound having 2 to 17 silicon atoms, comprising units of formula (I), and, optionally,
(E) additives.

Examples of radicals R$^3$ are the examples given above for R and R$^1$, preference being given to optionally substituted hydrocarbon radicals of 1 to 8 carbon atoms and more preferably to the methyl, vinyl, phenyl and 3,3,3-trifluoropropyl radical.

Alkyl radicals, especially methyl radicals, are bonded to at least 70 mol-% of the Si atoms present in the organopolysiloxane comprising units of formula (II). If the organopolysiloxanes (A) contain not only Si-bonded methyl and/or 3,3,3-trifluoropropyl radicals but also Si-bonded vinyl and/or phenyl radicals, then the latter are present in quantities of 0.001–30 mol-%.

The organopolysiloxanes (A) consists predominantly of diorganosiloxane units. The end groups of the organopolysiloxanes (A) can be trialkylsiloxy groups, especially the trimethylsiloxy radical or the dimethylvinylsiloxy radical; however, it is possible for one or more of these alkyl groups to be replaced by hydroxyl groups or alkoxy groups, such as methoxy or ethoxy radicals.

The organopolysiloxanes (A) can be liquids or highly viscous substances. The organopolysiloxanes (A) preferably have a viscosity at 25° C. of between 10$^3$ and 10$^8$ mm$^2$/s.

Examples of reinforcing fillers are pyrogenic or precipitated silicas having BET surface areas of at least 50 m$^2$/g, and also furnace black and acetylene black.

The silica fillers mentioned can be hydrophilic in nature or are hydrophobicized by known methods. Reference may be made, to DE 38 39 900 A (Wacker-Chemie GmbH; filed on Nov. 25, 1988) and to corresponding U.S. Pat. No. 5,057,151. Hydrophobicization is carried out with from 1% to 20% by weight of hexamethyldisilazane and/or divinyltetramethyldisilazane and from 0.5% to 5% by weight of water, based on the overall weight of the organopolysiloxane composition, these reagents being added to the charged organopolysiloxane in an appropriate mixing device, for example a compounder or internal mixer, before incorporating the hydrophilic silica successively into the composition.

Examples of nonreinforcing fillers are quartz flour, diatomaceous earth, calcium silicate, zirconium silicate, zeolites, metal oxide powders, such as aluminum oxide, titanium oxide, iron oxide or zinc oxide, barium silicate, barium sulfate, calcium carbonate, gypsum and also polymer powders, such as polyacrylonitrile powder or polytetrafluoroethylene powder. Other fillers which can be used are fibrous components, such as glass fibers and polymer fibers. The BET surface area of these fillers is preferably below 50 m$^2$/g.

The organopolysiloxane compositions which can be crosslinked to form elastomers contain filler (B) in quantities of from 1 to 200 parts by weight, preferably from 30 to 100 parts by weight, based on 100 parts by weight of organopolysiloxane (A).

The component (C) can comprise, an agent which initiates or brings about the crosslinking, and which have been used in peroxidically crosslinkable compositions.

Preferably, as component (C) in the organopolysiloxane compositions, use is made of peroxides, such as dibenzoyl peroxide, bis(2,4-dichlorobenzoyl) peroxide, dicumyl peroxide and 2,5-bis(tert-butylperoxy)-2,5-dimethylhexane, and of mixtures thereof, preference being given to bis(2,4-dichlorobenzoyl) peroxide and dicumyl peroxide.

The organopolysiloxane compositions which can be crosslinked to form elastomers contain peroxide (C) in quantities of from 0.4% to 2.0% by weight, preferably from 0.7% to 1.5% by weight, based on the overall weight of the organopolysiloxane composition.

The organopolysiloxane compositions which can be crosslinked to form elastomers contain organosilicon compound (D) in quantities of from 0.01% to 10.0% by weight, preferably from 0.05% to 2.0% by weight, based on the overall weight of the organopolysiloxane composition.

In accordance with the respective application, it is possible to add, to the organopolysiloxane compositions which can be vulcanized to form elastomers, additives (E), such as, processing auxiliaries, plasticizers, pigments and heat stabilizers.

Examples of plasticizers which can be used as additives (E) are polydimethylsiloxanes which are terminated with trimethylsilyl groups or hydroxyl groups and have a viscosity of not more than 1000 mm$^2$/s at 25° C., or else diphenylsilanediol.

Examples of heat stabilizers which can be used as additives (E) are transition metal fatty acid salts, such as iron octoate, transition metal silanolates, such as iron silanolate, and cerium(IV) compounds.

The compositions according to the present invention preferably contain no further substances.

The respective components used in preparing the compositions may comprise a single type of a component or a mixture of different types of components.

The peroxidically crosslinkable organopolysiloxane compositions can be prepared by known methods, for example by simple mixing of the individual components. The incorporation of the organosilicon compounds used in accordance with the invention can be carried out by various methods of admixture, for example in any desired step of mixing the individual components of the silicone rubber composition. In order to prepare the peroxidically crosslinkable compositions, the organosilicon compounds are mixed into the composition during the incorporation of the filler. Another option is to apply the organosilicon compound to the filler by mixing in a powder mixer or by mixing in a suspension of filler, inert organic solvent and organosilicon compound, and then stripping off the organic solvent to dryness, before incorporating together with the filler as carrier. Another option is to produce the organosilicon compound on the filler by chemical reaction, for example by analogy with the above-described process variant 2.

The peroxidically crosslinkable compositions can be crosslinked under the same conditions as for the peroxidically crosslinkable compositions known to date.

The peroxidically crosslinkable compositions have the advantage that the elastomers produced therefrom exhibit very good mechanical properties, especially in relation to tear propagation resistance and compression set.

The organopolysiloxane compositions and the elastomers produced therefrom can be used for all purposes for which organopolysiloxane compositions which can be crosslinked to form elastomers, or the elastomers themselves, have been used to date. The organopolysiloxane compositions and the elastomers produced are suitable for applications where enhanced tear propagation resistance is required, for example hoses, cable sheathing, automotive components and seals.

The addition-crosslinkable organopolysiloxane compositions comprise
(1) organopolysiloxanes having at least 18 silicon atoms and containing radicals with aliphatic carbon-carbon multiple bonds,
(2) organopolysiloxanes having Si-bonded hydrogen atoms,
(3) catalyst which promotes the addition of Si-bonded hydrogen onto aliphatic multiple bond,
(4) at least one aliphatically unsaturated organosilicon compound having 2 to 17 silicon atoms, comprising units of formula (I), and
(5) reinforcing and/or nonreinforcing fillers and, optionally, further substances.

Where the composition is an addition-crosslinking 2-component silicone rubber composition, the two components of the silicone rubber compositions can include all constituents in any desired combinations and proportions, with the proviso that one component does not include the constituents (1), (2) and (3).

The organopolysiloxanes (1) are linear, cyclic or branched siloxanes having at least 18 silicon atoms, comprising units of the formula

  (III), where
$R^4$ is identical or different and has a meaning given for $R^1$,
$R^5$ is identical or different and has a meaning given for R,
s is 0, 1 or 2, and
t is 0, 1, 2 or 3, with the proviso that the sum s+t is less than or equal to 3 and at least two radicals $R^4$ are present per molecule.

The organopolysiloxanes (1) have an average viscosity of from $10^2$ to $10^6$ mm$^2$/s at 25° C.

Examples of radical $R_4$ are the examples given for $R^1$ and also aliphatically unsaturated radicals which are accessible to a hydrosilylation reaction with an SiH-functional compound.

Radical $R^4$ comprises hydrocarbon radicals having an aliphatic multiple bond with 2 to 6 carbon atoms, such as vinyl, allyl, methallyl, 1-propenyl, 1-butenyl, 1-pentenyl radical, 5-hexenyl, butadienyl, hexadienyl, cyclopentenyl, cyclopentadienyl, cyclohexenyl, ethynyl, propargyl and 1-propynyl radical, the vinyl and allyl radical being more preferred.

Examples of radicals $R^5$ are the examples given for radical R.

Radical $R^5$ comprises optionally substituted, aliphatically saturated, monovalent hydrocarbon radicals of 1 to 8 carbon atoms, the methyl radical being preferred.

The organopolysiloxanes (1) are linear organopolysiloxanes having a viscosity of from 200 to $10^5$ mm$^2$/s at 25° C., of the structure (ViMe$_2$SiO$_{1/2}$)(ViMeSiO)$_{0-50}$(Me$_2$SiO)$_{30-2000}$(ViMe$_2$SiO$_{1/2}$), where Me is methyl radical and Vi is vinyl radical.

As organopolysiloxanes (2) which have Si-bonded hydrogen atoms, it is preferred to use linear, cyclic or branched siloxanes comprising units of the formula

  (IV)

where
$R^5$ is identical or different and has the meaning given above,
u is 0, 1, 2 or 3, and
v is 0, 1 or 2,
with the proviso that the sum of u+v is less than or equal to 3 and on average there are at least two Si-bonded hydrogen atoms per molecule.

The organopolysiloxanes (2) have an average viscosity of from 10 to 2·$10^4$ mm$^2$/s at 25° C.

Preference is given to the use of a polyorganosiloxane (2) containing three or more SiH bonds per molecule. When a constituent (2) is used which contains only two SiH bonds per molecule, the alkenyl-containing polyorganosiloxane (1) includes at least three alkenyl groups per molecule.

The polyorganosiloxane (2) is used as crosslinking agent The hydrogen content of the crosslinking agent, which relates exclusively to the hydrogen atoms bonded directly to silicon atoms, is in the range from 0.002% to 1.7% by weight of hydrogen, preferably between 0.1% and 1.7% by weight of hydrogen.

The organopolysiloxanes (2) are organopolysiloxanes having a viscosity of from 20 to 1000 mm$^2$/s at 25° C.

The polyorganosiloxane (2) is present in the curable silicone rubber composition in a quantity such that the molar ratio of SiH groups to radicals with aliphatic carbon-carbon multiple bond of the component (1) is between 0.5 and 5, preferably between 1.0 and 3.0.

Constituent (3) serves as catalyst for the addition reaction (hydrosilylation) between the radicals with aliphatic carbon-carbon multiple bond of the constituent (1) and the Si-bonded hydrogen atoms of the constituent (2). The literature has already described numerous suitable hydrosilylation catalysts. It is possible in the compositions of the present invention to use all hydrosilylation catalysts which are customarily used in addition-crosslinking silicone rubber compositions.

As hydrosilylation catalyst it is possible to use metals, such as platinum, rhodium, palladium, ruthenium and iridium, preferably platinum, fixed optionally on finely divided support materials, such as active charcoal, aluminum oxide or silicon dioxide.

Preference is given to the use of platinum and platinum compounds. Used are those platinum compounds which are soluble in polyorganosiloxanes. Soluble platinum compounds which can be used are, for example, the platinum-olefin complexes of the formulae (PtCl$_2$.olefin)$_2$ and H(PtCl$_3$.olefin), preferably used alkenes of 2 to 8 carbon atoms, such as ethylene, propylene, isomers of butene and of octene, or cycloalkenes of 5 to 7 carbon atoms, such as cyclopentene, cyclohexene and cycloheptene. Further soluble platinum catalysts are the platinum-cyclopropane complex of the formula (PtCl$_2$.C$_3$H$_6$)$_2$, the reaction products of hexachloroplatinic acid with alcohols, ethers and aldehydes or mixtures thereof, of the reaction product of hexachloroplatinic acid with methylvinylcyclotetrasiloxane in the presence of sodium bicarbonate in ethanolic solution. Complexes of platinum with vinylsiloxanes, such as 1,3-divinyltetramethyldisiloxane, are preferred.

The hydrosilylation catalyst can also be used in microencapsulated form, in which case the solid which envelops the catalyst, is finely divided and is insoluble in the polyorganosiloxane is, for example, a thermoplastic (polyester resins, silicone resins). The hydrosilylation catalyst can also be used in the form of an inclusion compound, for example in a cyclodextrin.

The quantity of hydrosilylation catalyst used depends on the desired rate of crosslinking and economic considerations. When customary platinum catalysts are used, the content of the curable silicone rubber composition relative to elemental platinum is in the range from 0.1 to 500 ppm by weight, preferably between 10 and 100 ppm by weight of elemental platinum.

The organopolysiloxane compositions which can be crosslinked to form elastomers comprise organosilicon compound (4) in quantities of from 0.01% to 10.0% by weight, preferably from 0.05% to 20% by weight, based on the overall weight of the organopolysiloxane composition.

Examples of fillers (5) used are reinforcing fillers having a specific surface area according to BET of at least 50 m$^2$/g, preferably 50–500 m$^2$/g, such as pyrogenically produced silica, silica hydrogels which have been dewatered while retaining their structure, i.e. aerogels, and other kinds of precipitated silicon dioxide; and nonreinforcing fillers having a specific surface area according to BET of less than 50 m$^2$/g, such as quartz flour, diatomaceous earth, calcium silicate, zirconium silicate, zeolites, clays, lithopones, metal oxides, such as iron oxide, zinc oxide, titanium dioxide and aluminum oxide, metal carbonates, such as calcium carbonate, magnesium carbonate and zinc carbonate, metal sulfates, such as barium sulfate, metal dusts, fibers, carbon black, graphite, mica and chalk. These fillers can be hydrophobicized.

The organopolysiloxane compositions which can be crosslinked to form elastomers comprise filler in quantities of from 1 to 50 parts by weight, preferably from 5 to 40 parts by weight, based on 100 parts by weight of the crosslinkable organopolysiloxane composition.

While the constituents (1) to (5) are necessary constituents of the silicone rubber composition, it is possible optionally for further additives to be present in the silicone rubber composition in a proportion of up to 50% by weight, preferably between 1% and 40% by weight These additives may be adhesion promoters, for example aminoalkoxysilanes and both linear and resinous methylsiloxanes containing Si-bonded hydrogen, heat stabilizers, for example transition metal fatty acid salts, such as iron octoate, transition metal silanolates, such as iron silanolate, cerium(IV) compounds, transition metal-containing silicic acids or palladium compounds, inhibitors, pigments, dyes and plasticizers.

Examples of plasticizers are diorganopolysiloxanes which are terminally blocked by triorganosiloxy groups and are liquid at room temperature, such as dimethylpolysiloxanes which are terminally blocked by trmethylsiloxy groups and have a viscosity of from 10 to 10,000 mm$^2$/s at 25° C., and organosiloxane resins which are liquid at room temperature.

Additives which may be present are those which serve for controlled establishment of the processing time (pot life) and rate of crosslinking of the curable silicone rubber composition. Examples of inhibitors, which are known, are acetylenic alcohols, such as ethynylcyclohexanol and 2-methyl-3-butyn-2-ol, trialkyl cyanurates, alkyl maleates, such as diallyl maleate and dimethyl maleate, alkyl fumarates, such as diethyl fumarate and diallyl fumarate, organic hydroperoxides, such as cumene hydroperoxide, tert-butyl hydroperoxide and pinane hydroperoxide, organic peroxides, benzotriazole, organic sulfoxides, organic amines and amides, phosphines, phosphites, nitrites, diaziridines and oximes.

The compositions contain no further substances.

The components used in preparing the compositions can comprise a single type of component, or a mixture of at least two different types of components.

The organopolysiloxane compositions which can be crosslinked by addition of Si-bonded hydrogen onto aliphatic carbon-carbon multiple bond can be prepared by known methods, for example by simple mixing of the individual components. Reference should be made to the German application, file reference P 4405245.6 cited above.

The incorporation of the organosilicon compounds used can be carried out by various methods of admixture, for example in any desired step of mixing of the individual components of the silicone rubber composition. In order to prepare the addition-crosslinkable compositions, the organosilicon compounds are mixed into the composition during the incorporation of the filler. Another option is to apply the organosilicon compound to the filler by mixing in a powder mixer or by mixing in a suspension of filler, inert organic solvent and organosilicon compound and stripping off the organic solvent to dryness, before incorporating with the filler as carrier. Another option is to produce the organosilicon compound on the filler by chemical reaction, for example by analogy with the above-described process variant 2.

When preparing the compositions in two components, the organosilicon compound with the invention is added in the last mixing step.

The compositions which can be crosslinked by addition can be cross-linked under the same conditions as for the addition-crosslinkable compositions known. The vulcanization is carried out at a temperature of from 10° to 200° C.

The addition-crosslinkable compositions have the advantage that they exhibit good rheological properties, and excellent stability of viscosity.

Moreover, the addition-crosslinkable compositions have the advantage that the elastomers produced exhibit good mechanical properties, especially in relation to tear propagation resistance and compression set.

The organopolysiloxane compositions and the elastomers produced can be used for all purposes. In particular, the organopolysiloxane compositions and the elastomers produced are suitable for articles shaped in accordance with the injection molding process, and impression applications which require improved tear propagation resistance, such as babies' pacifiers, nipples, seals and special molds.

In the examples described below, all viscosity data relate to a temperature of 25° C. Unless specified otherwise, the examples are carried out at the pressure of the surrounding atmosphere of about 1000 hPa, and at room temperature of 20° C., or at the temperature which is established when the reactants are combined at room temperature without additional heating or cooling. All parts and percentages are by weight unless specified otherwise.

The tear propagation resistance of the vulcanizates is determined in accordance with ASTM D 624-B-91.

The compression set is determined in accordance with DIN 53517.

The following abbreviations are used:
Me: Methyl radical
Et: Ethyl radical
Vi: Vinyl radical

EXAMPLE 1

Preparation of $(Me_2ViSiO)_2Si(Me_3SiO)_2$

Short form: $(VM)_2QM_2$

A mixture of 2007.2 g (10.8 mol) of 1,3-divinyltetramethyldisiloxane, 614.8 g (3.62 mol) of $SiCl_4$, 2.7 g (1000 ppm) of tetramethylurea and 231 g of $PNCl_2$ (25% strength in trichloropropane) (=2.2% $PNCl_2$) is stirred at room temperature for 5 hours (at the beginning, there is an exotherm to 62° C.). After the volatile constituents have been stripped off at 120° C. on a rotary evaporator under an oil pump vacuum, the residue is distilled. 180 g of pure $(Me_2ViSiO)_2SiCl_2$ are obtained as a colorless, clear liquid with a boiling point of 47° C. at 100 hPa. Identification is made via the $^1H$- and $^{29}Si$-NMR spectrum. The yield is 16.6%.

50.0 g (0.166 mol) of the $(Me_2ViSiO)_2SiCl_2$ thus obtained are then mixed with 41.9 g (0.415 mol) of triethylamine and 150 g of n-hexane, and 42.0 g (0.38 mol) of trimethylsilanol (technical-grade, dried over molecular sieve 0.4 nm; contains 19% hexamethyldisiloxane according to $^1H$-NMR) are added at room temperature over the course of 30 minutes. The mixture is left to react for one hour and then washed with water, and the organic phase is dried over sodium sulfate. After the volatile constituents have been stripped off at 25° C. on a rotary evaporator under an oil pump vacuum, the residue is fractionated using a Vigreux column. 25 g of pure $(Me_2ViSiO)_2Si(Me_3SiO)_2$ are obtained as a colorless, clear liquid with a boiling point of 58–62° C. at 300 hPa. Identification is made by means of the $^1H$-NMR spectrum. The yield is 37%.

EXAMPLE 2

Preparation of $(Me_2ViSiO)_3Si$—OH

Short form: $(VM)_3Q$—OH

A mixture of 1834 g (9.86 mol) of 1,3-divinyltetramethyldisiloxane, 559 g (3.29 mol) of $SiCl_4$, 2.4 g (25 ppm) of tetramethylurea (2.5% strength in n-hexane) and 24 g of $PNCl_2$ (25% strength in trichloropropane) (=0.25% $PNCl_2$) is stirred at room temperature for 46 hours. After the volatile constituents have been stripped off at 30° C./400 hPa on a rotary evaporator, the residue is distilled. 334 g of a colorless, clear liquid with a boiling point of 93–100° C. at 600 hPa are obtained. The composition of the product obtained is determined by means of the $^{29}Si$-NMR spectrum:

94 mol-% $(Me_2ViSiO)_3SiCl$ and;

6 mol-% $(Me_2ViSiO)_4Si$;

The yield is 26%.

348 g (0.95 mol) of the resulting mixture of 94 mol-% $(Me_2ViSiO)_3SiCl$ and 6 mol-% $(Me_2ViSiO)_4Si$ are then mixed with 105.7 g (1.05 mol) of triethylamine and 1670 g of n-hexane, and 84.9 g (4.7 mol) of water are added at room temperature. The mixture is stirred at room temperature for 18 hours, then refluxed for one hour and washed with water, and the organic phase is dried over sodium sulfate. After the volatile constituents have been stripped off at 30° C./700 hPa on a rotary evaporator, the residue is distilled using a packed column. 267 g of a colorless, clear liquid with a boiling point of 73–75° C. at 500 hPa are obtained. The composition of the product obtained is determined by means of the $^{29}Si$-NMR spectrum:

96 mol-% $(Me_2ViSiO)_3SiOH$ and;

4 mol-% $(Me_2ViSiO)_4Si$.

EXAMPLE 3

Preparation of $(Me_2ViSiO)_3Si(Me_3SiO)$

Short form: $(VM)_3QM$ 45.0 g (0.174 mol) of the $(Me_2ViSiO)_3SiOH$ (96% pure) obtained in Example 2 are added dropwise over the course of 40 minutes to a mixture of 23.8 g (0.21 mol) of trimethylchlorosilane, 26.3 g (0.26 mol) of triethylamine and 150 g of n-hexane at room temperature. The mixture is allowed to react for one hour and washed with water, and the organic phase is dried over sodium sulfate. After the volatile constituents have been stripped off at 25° C. on a rotary evaporator under an oil pump vacuum, the residue is fractionated using a Vigreux column. 15 g of pure $(Me_2ViSiO)_3Si(Me_3SiO)$ are obtained as a colorless, clear liquid with a boiling point of 60–63° C. at 400 hPa. Identification is made by means of the $^1H$-NMR spectrum. The yield is 28%.

EXAMPLE 4

Preparation of $(Me_2ViSiO)_2(Me_3SiO)SiOH$
Short form: $(VM)_2MQ$—OH

A solution of 19 g (0.19 mol) of trimethylsilanol (technical-grade, dried over molecular sieve 0.4 nm; contains 10% hexamethyldisiloxane according to $^1$H-NMR) is added dropwise over the course of 225 hours at room temperature to a mixture of 58.5 g (0.19 mol) of $(Me_2ViSiO)_2SiCl_2$, whose preparation is described above in Example 1, 20.8 g (0.2 mol) of triethylamine and 292 g of tetrahydrofuran. The mixture is left to react for 2 hours, filtered over a filtration aid (commercially available under the name "Seitz Super" from Seitz Filterwerke, Bad Kreuznach, Germany) and the solvent is distilled off at 30° C. and 700 hPa. After refiltration, distillation is carried out over a bridge. In the boiling range of 55–81° C. at 500 hPa, 41.5 g of a colorless, clear liquid are obtained which according to $^{29}$Si-NMR spectrum contains 83 mol-% $(Me_2ViSiO)_2(Me_3SiO)SiCl$. The yield is 51%. A solution of 58.0 g (0.11 mol) of the resulting $(Me_2ViSiO)_2(Me_3SiO)SiCl$ in 60 g of diethyl ether is added dropwise over the course of 60 minutes at room temperature to a mixture of 29 g (1.6 mol) of water, 31.9 g (0.32 mol) of triethylamine and 203 g of diethyl ether, in the course of which the temperature of the reaction mixture rises to 30° C. The mixture is left to react for 2 hours and washed with water, and the organic phase is dried over sodium sulfate. After the volatile constituents have been stripped off at 25–60° C. on a rotary evaporator under an oil pump vacuum, 47 g of a clear oil are obtained as residue. According to $^1$H- and $^{29}$Si-NMR spectrum, the oil shows a content of $(Me_2ViSiO)_2(Me_3SiO)SiOH$ of about 80%. Residual amounts of triethylamine are removed by filtration over acid-activated bleaching earth (commercially available under the name "Tonsil Optimum FF" from Suidchemie AG, Munich). 33 g of $(Me_2ViSiO)_2(Me_3SiO)SiOH$ are obtained; the yield is about 90%.

EXAMPLE 5

Preparation of $(Me_2ViSiO)_4Si$
Short form: $(VM)_4Q$ 848 g of ethanol are added slowly to a mixture of 248 g of $SiCl_4$ and 1540 g of vinyldimethylchlorosilane, and this mixture is hydrolyzed slowly with 360 g of water. Following the addition of 400 g of water, the mixture is stirred for 90 minutes. The aqueous phase is separated off and the organic phase is washed three times with water. The organic phase is then distilled to 130° C. under a pressure of 70 hPa. 570 g of a clear liquid are obtained, which contains 95% $(ViMe_2SiO)_4Si$ according to its gas chromatogram.

EXAMPLE 6

Preparation of $(Me_2ViSiO)_2Si(Me_3SiO)_2$-60%
Short form: $(VM)_2QM_2$-60%

848 g of ethanol are added slowly to a mixture of 248 g of $SiCl_4$, 770 g of vinyldimethylchlorosilane and 694 g of trimethylchlorosilane, and the mixture is hydrolyzed slowly with 360 g of water. Following the addition of 400 g of water, the mixture is stirred for 90 minutes. The aqueous phase is separated off and the organic phase is washed three times with water. The organic phase is distilled to 130° C. under a pressure of 300 hPa. 525 g of a liquid residue are obtained, which contains 5% $(Me_3SiO)_4Si$, 18% $(Me_2ViSiO)Si(Me_3SiO)_3$, 60% $(Me_2ViSiO)_2Si(Me_3SiO)_2$, 14% $(Me_2ViSiO)_3Si(MeiO)$ and 3% $(ViMe_2SiO)_4Si$ according to its gas chromatogram.

EXAMPLE 7

Preparation of $(Me_2ViSiO)_2Si(Me_3SiO)_2$-55%
Short form: $(VM)_2QM_2$-55%

848 g of ethanol are added slowly to a mixture of 248 g of $SiCl_4$, and 1388 g of trimethylchlorosilane, and hydrolysis is carried out slowly with 360 g of water. Following the addition of 400 g of water, the mixture is stirred for 90 minutes. The aqueous phase is separated off and the organic phase is washed three times with water. The organic phase is distilled to 130° C. under a pressure of 70 hPa. 200 g of the resulting liquid are dissolved in 212 g of 1,3-divinyltetramethyldisiloxane and the solution is treated over a period of 6 hours at 80° C. with the addition of 30 g of acid-activated bleaching earth (commercially available under the name "Tonsil Optimum FF" from Südchemie AG, Munich). Following removal of the catalyst by filtration, the solution is distilled at 130° C. and at a pressure of 300 hPa. 208 g of a liquid residue are obtained which contains 5% $(Me_3SiO)_4Si$, 20% $(Me_2ViSiO)Si(Me_3SiO)_3$, 55% $(Me_2ViSiO)_2Si(Me_3SiO)_2$, 16% $(Me_2ViSiO)_3Si(Me_3SiO)$ and 4% $(ViMe_2SiO)_4Si$ according to its gas chromatogram.

EXAMPLE 8

Preparation of a Siloxane of Composition
$[Me_2ViSiO]_4[Me_3SiO]_4[SiO_{4/2}]_3$
Short form: $[(VM)_{1.3}M_{1.3}Q]$ 848 g of ethanol are added slowly to a mixture of 248 g of $SiCl_4$, 250 g of vinyldimethylchlorosilane and 225 g of trimethylchlorosilane, and the mixture is slowly hydrolyzed with 360 g of water. Following the addition of 400 g of water, the mixture is stirred for 90 minutes. The aqueous phase is separated off and the organic phase is washed three times with water. The organic phase is then distilled to 130° C. at a pressure of 70 hPa. 462 g of a liquid residue with a viscosity of 14 mm$^2$/s are obtained, which according to its $^{29}$Si-NMR spectrum has a molar ratio of vinyldimethylsiloxy units to $SiO_{4/2}$ units of 1.30 to 1 and of trimethylsiloxy units to $SiO_{4/2}$ units of 1.32 to 1.

EXAMPLE 9

Preparation of a Siloxane of Composition
$[Me_2ViSiO]_4[Me_3SiO]_4[SiO_{4/2}]_3$
Short form: $[(VM)_{1.3}M_{1.3}Q]$ 848 g of ethanol are added slowly to a mixture of 248 g of $SiCl_4$ and 500 g of trimethylchlorosilane, and the mixture is slowly hydrolyzed with 360 g of water. Following the addition of 400 g of water, the mixture is stirred for 90 minutes. The aqueous phase is separated off and the organic phase is washed three times with water. The organic phase is then distilled to 130° C. at a pressure of 70 hPa. 300 g of the resulting liquid are dissolved in 212 g of hexamethyldisiloxane and the solution is treated over a period of 6 hours at 80° C. with addition of 30 g of acid-activated bleaching earth (commercially available under the name "Tonsil Optimum FF" from Südchemie AG, Munich). The catalyst is removed by filtration and the solution is distilled at 130° C. and a pressure of 300 hPa. 317 g of a liquid residue with a viscosity of 13.5 mm$^2$/s are obtained, which according to its $^{29}$Si-NMR spectrum has a molar ratio of vinyldimethylsiloxy units to $SiO_{4/2}$ units of 1.31 to 1 and of trimethylsiloxy units to $SiO_{4/2}$ units of 1.29 to 1.

EXAMPLE 10

Preparation of (ViMe$_2$SiO)$_3$SiOH

Short form: (VM)$_3$QOH 50 g of water and 50 g of 1,3-divinyl-1,1,3,3-tetramethyldisilazane are mixed with 100 g of a pyrogenic silica having a specific surface area according to BET of 300 m$^2$/g (commercially available under the name "WACKER HDK® T30" from Wacker-Chemie GmbH), and the mixture is stirred at room temperature for one hour and stored at 80° C. for 24 hours. The pulverulent reaction mixture is then purified at 140° C. for 2 hours in a weak stream of nitrogen in order to remove readily volatile compounds. Distillative expulsion in dry nitrogen at 200° C. for 8 hours gives, after separation of a small amount of an aqueous phase, 16.8 g of a clear liquid which according to gas chromatography contains 82% (VM)$_3$QOH.

EXAMPLE 11

Preparation of (ViMe$_2$SiO)$_3$SiOH

Short form: (VM$_3$QOH

The procedure described in Example 10 is repeated with the modification that the process is terminated after the purification in a weak stream of nitrogen to remove readily volatile compounds, and no subsequent distillative expulsion in dry nitrogen is carried out. A white powder is obtained with a content of volatile compounds (determined as the weight loss after heating for 2 hours under a gentle stream of nitrogen at 230° C.) of 13.7%. These volatile compounds contain, according to gas chromatography and in addition to 13% water, 71% (VM)$_3$QOH.

EXAMPLE 12

Preparation of (ViMe$_2$SiO)$_3$SiOH

Short form: (VM)$_3$QOH 50 g of water, 50 g of 1,3-divinyl-1,1,3,3-tetramethyldisilazane and 100 g of a pyrogenic silica having a specific surface area according to BET of 300 m$^2$/g (commercially available under the name "WACKER HDK® T30" from Wacker-Chemie GmbH) are suspended in 500 g of hexamethyldisiloxane and then reacted at 80° C. for 24 hours. Excess hexamethyldisiloxane is then distilled off under atmospheric pressure at 110° C. The pulverulent reaction mixture obtained is purified at 140° C. for 2 hours in a weak stream of nitrogen in order to remove readily volatile compounds. Distillative expulsion in dry nitrogen at 200° C. for 8 hours gives, after separation of a small amount of an aqueous phase, 14.7 g of a clear liquid which according to gas chromatography contains 80% (VM)$_3$QOH.

EXAMPLE 13

Preparation of (ViMe$_2$SiO)$_3$SiOH

Short form: (VM)$_3$QOH

The procedure described in Example 12 is repeated with the modification that the process is terminated after the purification in a weak stream of nitrogen to remove readily volatile compounds, and no subsequent distillative expulsion in dry nitrogen is carried out A white powder is obtained with a content of volatile compounds (determined as the weight loss after heating for 2 hours under a gentle stream of nitrogen at 230° C.) of 13.9%. These volatile compounds contain, according to gas chromatography and in addition to 11% water, 68% (VM)$_3$QOH.

EXAMPLE 14

Preparation of (ViMe$_2$SiO)$_3$SiMe

Short form: (VM)$_3$T(Me)

The procedure described in Example 5 is repeated with the modification that, instead of 248 g of SiCl$_4$, 218 g of methyltrichlorosilane are used. 460 g of a colorless liquid are obtained which according to gas chromatography contains 91% (ViMe$_2$SiO)$_3$SiMe.

EXAMPLE 15

Preparation of (ViMe$_2$SiO)$_3$SiVi

Short form: (VM)$_3$T(Vi)

The procedure described in Example 5 is repeated with the modification that instead of 248 g of SiCl$_4$, 236 g of vinyltrichlorosilane are used. 435 g of a colorless liquid are obtained which according to gas chromatography contains 92% (ViMe$_2$SiO)$_3$SiVi.

EXAMPLE 16

Preparation of a Basic Mass for Addition-crosslinking Compositions 500 g of a vinyl-terminated dimethyl polysiloxane with a viscosity of 20,000 mm$^2$/s are placed in a 5 liter laboratory kneading apparatus and heated to 150° C., and 390 g of a filler are added, this filler being a silica which has been hydrophobicized using hexamethyldisilazane in accordance with DE 38 39 900 A, mentioned above. Volatile constituents are removed by kneading at 150° C. and 1000 hPa for one hour. A stiff mass is produced which is diluted with 410 g of the above mentioned dimethylpolysiloxane. An A component and a B component are produced from this basic mass in a planetary mixer.

To produce the A component, 380 g of the above-described basic mass, 0.2 g of Pt complex with divinyltetramethyldisiloxane, 0.6 g of the organosilicon compounds indicated in Table 1, whose preparation is described in the foregoing examples, and 1.0 g of ethynyl-cyclohexanol as inhibitor are mixed at room temperature and atmospheric pressure over a period of 30 minutes.

To produce the B component, 380 g of the above-described basic mass, 18 g of linear methyl-H-polysiloxane with 0.5 mol-% of Si—H and a viscosity of 400 mm$^2$/s as crosslinking agent, 1.0 g of ethynylcyclohexanol as inhibitor and 0.6 g of the low molecular mass organosilicon compounds indicated in Table 1, whose preparation is described in the foregoing examples, are mixed at room temperature and atmospheric pressure over a period of 30 minutes.

Components A and B are each mixed in a weight ratio of 1:1 and left to crosslink at a temperature of 160° C.

After vulcanization and 4 hours of thermal conditioning at 200° C., the tear propagation resistance and the compression set are determined. The results are given in Table 1.

TABLE 1

| organosilicon compound according to Example | short form | tear propagation resistance in N/mm | compression set in % |
|---|---|---|---|
| 1 | (VM)$_2$M$_2$Q | 37 | 17 |
| 2 | (VM)$_3$QOH | 40 | 15 |
| 3 | (VM)$_3$MQ | 39 | 15 |
| 4 | (VM)$_2$MQOH | 38 | 18 |
| 5 | (VM)$_4$Q | 44 | 11 |

TABLE 1-continued

| organosilicon compound according to Example | short form | tear propagation resistance in N/mm | compression set in % |
|---|---|---|---|
| 6 | (VM)$_2$M$_2$Q-60 | 37 | 20 |
| 7 | (VM)$_2$M$_2$Q-55 | 37 | 20 |
| 8 | (VM)$_{1.3}$M$_{1.3}$Q | 36 | 23 |
| 9 | (VM)$_{1.3}$M$_{1.3}$Q | 36 | 23 |
| 10 | (VM)$_3$QOH | 39 | 15 |
| 12 | (VM)$_3$QOH | 39 | 15 |
| 14 | (VM)$_3$T(Me) | 40 | 14 |
| 15 | (VM)$_3$T(Vi) | 43 | 13 |
| C1 | — | 31 | 33 |

EXAMPLE 17

The procedure for producing the basic mass described in Example 16 is repeated with the modification that the filler employed is 385 g of hydrophobicized silica rather than 390 g.

To produce the A component, 380 g of the above-described basic mass, 0.2 g of platinum complex with divinyltetramethyldisiloxane, 0.6 g of the pulverulent product indicated in Table 2, containing the organosilicon compounds, whose preparation is described in the examples mentioned, and 1.0 g of ethynylcyclohexanol as inhibitor are mixed at room temperature and atmospheric pressure over a period of 30 minutes.

To produce the B component, 380 g of the above-described basic mass, 18 g of linear methyl-H-polysiloxane with 0.5 mol-% of Si—H and a viscosity of 400 mm$^2$/s as crosslinking agent, 1.0 g of ethynylcyclohexanol as inhibitor and 5 g of the pulverulent product indicated in Table 2, containing the organosilicon compounds, whose preparation is described in the foregoing examples, are mixed at room temperature and atmospheric pressure over a period of 30 minutes.

The procedure is as described in Example 16. After vulcanization and 4 hours of thermal conditioning at 200° C., the tear propagation resistance and the compression set are determined. The results are given in Table 2.

TABLE 2

| organosilicon compound according to Example | short form | tear propagation resistance in N/mm | compression set in % |
|---|---|---|---|
| 11 | (VM)$_3$QOH | 39 | 16 |
| 13 | (VM)$_3$QOH | 38 | 15 |

Comparison Example 1

The procedure described in Example 16 is repeated with the modification that in each case no organosilicon compound is used to prepare either the A or the B component The results are given in Table 1.

What is claimed is:

1. A peroxidically crosslinkable composition comprising:
(A) organopolysiloxanes comprising units of the formula $$R^3_r SiO_{\frac{4-r}{2}} \qquad (II)$$

in which
R$^3$ is identical or different and is an optionally substituted hydrocarbon radical, and
r is 0, 1, 2 or 3 and has an average numerical value of from 1.9 to 2.1,
(B) reinforcing filler, nonreinforcing fillers, or mixtures thereof,
(C) an agent which promotes crosslinking, and
(D) at least one organosilicon compound having 2 to 17 silicon atoms, comprising units of the formula $$R_a R^1_b (OR^2)_c SiO_{4-(a+b+c)/2} \qquad (I),$$

where
R is identical or different and is a hydrogen atom or an optionally substituted, SiC-bonded aliphatically saturated hydrocarbon radical of 1 to 18 carbon atoms, with the proviso that not more than one R radical per silicon atom is a hydrogen atom,
R$^1$ is identical or different and is SiC-bonded, aliphatically unsaturated hydrocarbon radical having 2 to 18 carbon atoms,
R$^2$ is identical or different and is a hydrogen atom or optionally substituted hydrocarbon radical having 1 to 18 carbon atoms, where the hydrocarbon radical is optionally interrupted by oxygen atoms,
a is 0, 1, 2, or 3,
b is 0, 1, 2 or 3,
c is 0, 1, 2 or 3,
where the sum of a, b and c is less than or equal to 3 and at least one radical R$^1$ is present per molecule, wherein (D) is present in a tear propagation resistance or compression set improving amount.

2. The peroxidically crosslinkable composition of claim 1 wherein at least one R$^2$ is present comprising a hydrogen atom.

3. A peroxidically crosslinkable composition as claimed in claim 1, wherein the organosilicon compound has at least two radicals R$^1$.

4. A peroxidically crosslinkable composition as claimed in claim 1, wherein the organosilicon compound has at least three radicals R$^1$.

5. A peroxidically crosslinkable composition as claimed in claim 1, wherein the organosilicon compound has a numerical ratio of M units to the sum of Q units and/or T units of greater than or equal to 2.

6. A peroxidically crosslinkable composition as claimed in claim 1 wherein said organosilicon compound comprises:
an organosilicon compound having 2 to 17 silicon atoms consisting of the units of the formula $$((R_3SiO)_g(R_2R^1SiO)_h(OH)_iSi)_2O \qquad (Ib),$$

where
g is 0, 1, 2 or 3,
h is 0, 1, 2 or 3,
i is 0, 1 or 2,
where the sum of g+h+i is equal to 3 for each silicon atom and there is at least one radical R$^1$ present per formula (Ib).

7. A peroxidically crosslinkable composition as claimed in claim 1, wherein the component (B) is present in quantities of from 1 to 200 parts by weight, based on 100 parts by weight of organopolysiloxane (A), component (C) is present in quantities of from 0.4% to 2.0% by weight, based on the overall weight of the organopolysiloxane composition, and component (D) is present in quantities of from 0.01% to 10.0% by weight, based on the overall weight of the organopolysiloxane composition.

8. An addition-crosslinkable composition comprising:
(1) organopolysiloxanes having at least 18 silicon atoms and containing radicals with aliphatic carbon-carbon multiple bonds, (2) organopolysiloxanes having Si-bonded hydrogen atoms, (3) catalyst which promotes the addition of Si-bonded hydrogen onto aliphatic multiple bond, and (4) at least one organosilicon compound having 2 to 17 silicon atoms, comprising units of the formula $$R_a R^1_b (OR^2)_c SiO_{4-(a+b+c)/2} \qquad (I),$$

where

R is identical or different and is a hydrogen atom or an optionally substituted, SiC-bonded aliphatically saturated hydrocarbon radical of 1 to 18 carbon atoms, with the proviso that not more than one R radical per silicon atom is a hydrogen atom, $R^1$ is identical or different and is SiC-bonded, aliphatically unsaturated hydrocarbon radical having 2 to 18 carbon atoms, $R^2$ is identical or different and is a hydrogen atom or optionally substituted hydrocarbon radical having 1 to 18 carbon atoms, where the hydrocarbon radical is optionally interrupted by oxygen atoms, a is 0, 1, 2 or 3, b is 0, 1, 2 or 3, c is 0, 1, 2 or 3, where the sum of a, b and c is less than or equal to 3 and at least one radical $R^1$ is present per molecule, wherein component (2) is present in a quantity such that the molar ratio of SiH groups to radicals with aliphatic carbon-carbon multiple bond of component (1) is between 0.5 and 5, and component (4) is present in quantities of from 0.01% to 10.0% by weight, based on the overall weight of the organopolysiloxane composition.

9. The addition-crosslinkable composition of claim 8 wherein at least one $R^2$ is present comprising a hydrogen atom.

10. An addition crosslinkable composition as claimed in claim 8, wherein the organosilicon compound has at least two radicals $R^1$.

11. An addition crosslinkable composition as claimed in claim 8, wherein the organosilicon compound has at least three radicals $R^1$.

12. An addition crosslinkable composition as claimed in claim 8, wherein the organosilicon compound has a numerical ratio of M units to the sum of Q units and/or T units of greater than or equal to 2.

13. An addition-crosslinkable composition as claimed in claim 8 wherein said organosilicon compound comprises:

an organosilicon compound having 2 to 17 silicon atoms consisting of the units of the formula $$((R_3SiO)_g(R_2R^1SiO)_h(OH)_iSi)_2O \qquad (Ib),$$

g is 0, 1, 2 or 3, h is 0, 1, 2, or 3, i is 0, 1 or 2, where the sum of g+h+i is equal to 3 for each silicon atom and there is at least one radical $R^1$ present per formula (Ib).

14. A peroxidically crosslinkable composition comprising:

(A) organopolysiloxanes comprising units of the formula $$R^3_r SiO_{\frac{4-r}{2}} \qquad (II)$$

in which $R^3$ is identical or different and is an optionally substituted hydrocarbon radical, and r is 0, 1, 2 or 3 and has an average numerical value of from 1.9 to 2.1, (B) reinforcing filler, nonreinforcing fillers, or mixtures thereof, (C) an agent which promotes crosslinking, and (D) at least one organosilicon compound having 2 to 17 silicon atoms, comprising units of the formula $$R_a R^1_b (OR^2)_c SiO_{4-(a+b+c)/2} \qquad (I),$$

where

R is identical or different and is a hydrogen atom or an optionally substituted, SiC-bonded aliphatically saturated hydrocarbon radical of 1 to 18 carbon atoms, with the proviso that not more than one R radical per silicon atom is a hydrogen atom, $R^1$ is identical or different and is SiC-bonded, aliphatically unsaturated hydrocarbon radical having 2 to 18 carbon atoms, $R^2$ is identical or different and is a hydrogen atom or optionally substituted hydrocarbon radical having 1 to 18 carbon atoms, where the hydrocarbon radical is optionally interrupted by oxygen atoms, a is 0, 1, 2, or 3, b is 0, 1, 2 or 3, c is 0, 1, 2 or 3, where the sum of a, b and c is less than or equal to 3 and at least one radical $R^1$ is present per molecule, wherein the component (B) is present in quantities of from 1 to 200 parts by weight, based on 100 parts by weight of organopolysiloxane (A), component (C) is present in quantities of from 0.4% to 2.0% by weight, based on the overall weight of the organopolysiloxane composition, and component (D) is present in quantities of from 0.01% to 10.0% by weight, based on the overall weight of the organopolysiloxane composition.

15. The peroxidically crosslinkable composition of claim 14 wherein at least one $R^2$ is present comprising a hydrogen atom.

16. A peroxidically crosslinkable composition as claimed in claim 14, wherein the organosilicon compound has at least two radicals $R^1$.

17. A peroxidically crosslinkable composition as claimed in claim 14, wherein the organosilicon compound has at least three radicals $R^1$.

18. A peroxidically crosslinkable composition as claimed in claim 14, wherein the organosilicon compound has a numerical ratio of M units to the sum of Q units and/or T units of greater than or equal to 2.

19. A peroxidically crosslinkable composition as claimed in claim 14, wherein said organosilicon compound comprises:

an organosilicon compound having 2 to 17 silicon atoms consisting of the units of the formula $$((R_3SiO)_g(R_2R^1SiO)_h(OH)_iSi)_2O \qquad (Ib),$$

where g is 0, 1, 2 or 3, h is 0, 1, 2 or 3, i is 0, 1 or 2, where the sum of g+h+i is equal to 3 for each silicon atom and there is at least one radical $R^1$ present per formula (Ib).

20. A peroxidically crosslinkable composition as claimed in claim 7, wherein the component (D) is present in quantities of from 0.05%–2.0% by weight, based on the overall weight of the organopolysiloxane composition.

21. A peroxidically crosslinkable composition as claimed in claim 14, wherein the component (D) is present in quantities of from 0.05%–2.0% by weight, based on the overall weight of the organopolysiloxane composition.

22. An addition-crosslinkable composition as claimed in claim 8, wherein the component (4) is present in quantities of from 0.05%–2.0% by weight, based on the overall weight of the organopolysiloxane composition.

23. The peroxidically crosslinkable composition of claim 1 wherein component (D) comprises a tear propagation resistance and compression set agent.

24. A method of increasing the tear propagation resistance and compression set of elastomers formed from crosslinkable compositions, said method comprising:

providing a crosslinkable composition comprising (1) organopolysiloxane; and adding to the crosslinkable composition a tear propagating resistance and compression set agent comprising at least one organosilicon compound having 2 to 17 silicon atoms, comprising units of the formula

where
R is identical or different and is a hydrogen atom or an optionally substituted, SiC-bonded aliphatically saturated hydrocarbon radical of 1 to 18 carbon atoms, with the proviso that not more than one R radical per silicon atom is a hydrogen atom, $R^1$ is identical or different and is SiC-bonded, aliphatically unsaturated hydrocarbon radical having 2 to 18 carbon atoms, $R^2$ is identical or different and is a hydrogen atom or optionally substituted hydrocarbon radical having 1 to 18 carbon atoms, where the hydrocarbon radical is optionally interrupted by oxygen atoms, a is 0, 1, 2, or 3,
b is 0, 1, 2 or 3,
c is 0, 1, 2 or 3, where the sum of a, b and c is less than or equal to 3 and at least one radical $R^1$ is present per molecule.

25. The method of claim 24, wherein the crosslinkable composition comprises a peroxidically crosslinkable composition, the peroxidically crosslinkable composition further comprising:

reinforcing filler, nonreinforcing fillers, and mixtures thereof; and an agent which promotes crosslinking, wherein the (1) organopolysiloxane comprises units of the formula

in which
$R^3$ is identical or different and is an optionally substituted hydrocarbon radical, and r is 0, 1, 2 or 3 and has an average numerical value of from 1.9 to 2.1.

26. The method of claim 24 wherein the crosslinkable composition comprises an addition crosslinkable composition further comprising:

organopolysiloxanes having Si-bonded hydrogen atoms, and catalyst which promotes the addition of Si-bonded hydrogen onto aliphatic multiple bond, wherein the (1) organopolysiloxanes have at least 18 silicon atoms and contain radicals with aliphatic carbon-carbon multiple bonds.

27. The method of claim 25 wherein the organosilicon compound is present in quantities of from about 0.01%–10.0% by weight, based on the overall weight of the organopolysiloxane composition.

28. The method of claim 26 wherein the organosilicon compound is present in quantities of from about 0.01%–10.0% by weight, based on the overall weight of the organopolysiloxane composition.

* * * * *